United States Patent [19]

Ishii et al.

[11] Patent Number: 5,328,903

[45] Date of Patent: Jul. 12, 1994

[54] COMPOSITION FOR SOLID PHARMACEUTICAL PREPARATIONS CONTAINING VITAMIN D3 DERIVATIVE

[75] Inventors: Kuniaki Ishii, Saitama; Yumiko Toriumi; Shigeru Itai, both of Ageo; Hidefumi Hayashi, Tokyo; Masami Nemoto, Okegawa, all of Japan

[73] Assignees: Taisho Pharmaceutical Co. Ltd.; Sumitomo Pharmaceuticals Co. Ltd., Japan; Wisconsin Alumni Research Foundation, Madison, Wis.

[21] Appl. No.: 16,576

[22] Filed: Feb. 10, 1993

Related U.S. Application Data

[63] Continuation of Ser. No. 691,352, Apr. 25, 1991, abandoned.

[30] Foreign Application Priority Data

Apr. 28, 1990 [JP] Japan ................................ 2-112269

[51] Int. Cl.$^5$ .................. A61K 31/595; A61K 31/58; A61K 9/36
[52] U.S. Cl. .................................... 514/168; 514/176; 514/780; 514/960; 514/961; 424/479; 424/480; 424/465; 552/653
[58] Field of Search ...................... 514/176, 780, 168; 424/479, 480, 465; 552/653

[56] References Cited

U.S. PATENT DOCUMENTS

| | | | |
|---|---|---|---|
| 3,852,421 | 12/1974 | Koyanagi et al. | 424/91 |
| 3,998,973 | 12/1976 | Carlson | 424/357 |
| 4,176,175 | 11/1979 | Maekawa et al. | 424/35 |
| 4,226,849 | 10/1980 | Schor | 424/19 |
| 4,412,986 | 11/1983 | Kawata et al. | 424/80 |
| 4,421,738 | 12/1983 | Yamagiwa et al. | 424/35 |
| 4,626,287 | 12/1986 | Shah et al. | 106/197.1 |
| 4,680,323 | 7/1987 | Lowey | 524/43 |
| 4,832,956 | 5/1989 | Gergely et al. | 424/466 |

FOREIGN PATENT DOCUMENTS

| | | |
|---|---|---|
| 0116755 | 8/1984 | European Pat. Off. . |
| 0215596 | 3/1987 | European Pat. Off. . |
| 0387808 | 9/1990 | European Pat. Off. . |
| 0413828 | 2/1991 | European Pat. Off. . |
| 57-126417 | 1/1981 | Japan . |

*Primary Examiner*—Marianne M. Cintins
*Assistant Examiner*—T. J. Griares
*Attorney, Agent, or Firm*—Andrus, Sceales, Starke & Sawall

[57] ABSTRACT

A composition for solid pharmaceutical preparations containing a vitamin $D_3$ derivative capable of permitting the derivative to be uniformly distributed in the composition while being stabilized. The composition contains an excipient consisting of mannitol and sugar, a degradative agent consisting of hydroxypropyl cellulose, and a binder consisting of polyvinyl pyrrolidone and hydroxypropylmethyl cellulose.

1 Claim, No Drawings

COMPOSITION FOR SOLID PHARMACEUTICAL PREPARATIONS CONTAINING VITAMIN D3 DERIVATIVE

This is a continuation application of U.S. application Ser. No. 691,352 filed Apr. 25, 1991, now abandoned.

BACKGROUND OF THE INVENTION

This invention relates to a composition for solid pharmaceutical preparations containing a vitamin $D_3$ derivative and a process for the preparation thereof, and more particularly to a composition for solid pharmaceutical preparations containing a vitamin $D_3$ derivative in which mannitol and sugar are used as an excipient.

In general, vitamin $D_3$ derivatives are labile and apt to be readily oxidized and cause isomerization. It is known that the isomerization of the derivatives readily occurs due to contact with an additive as well as exposure to light and heat (Tetsuya Takahashi and Ryuichi Yamamoto, Journal of the Pharmaceutical Society of Japan, 89, 909 (1969)). Also, in order to stabilize a vitamin $D_3$ derivative, techniques of incorporating the vitamin D derivative in bile acids, cholesterols or polyvinyl pyrrolidone to prevent oxidation and isomerization of the derivative are proposed (Japanese Patent Application Laid-Open Publication No. 69562/1980, Japanese Patent Application Laid-Open Publication No. 40461/1982, Japanese Patent Application Laid-Open Publication No. 206533/1983 and Japanese Patent Application Laid-Open Publication No. 155309/1984).

As will be noted from the above, vitamin $D_3$ derivatives are labile to heat and light and apt to be readily oxidized, so that a suitable means such as refrigeration, light shielding, replacement with inert gas or the like is employed to prevent deterioration of pharmaceutical preparations containing a vitamin $D_3$ derivative.

In particular, 26, 26, 26, 27, 27, 27-hexafluoro-1α, 25-dihydroxycholecalciferol (Kobayashi et al, Chem. Pharm. Bull, 30, 4297 (1982)) prepared by replacing each of six hydrogen atoms at positions 26 and 27 of 1α, 25-dihydroxycholecalciferol with a fluorine atom has a extremely high vitamin D-like activity and is merely contained in a very small amount in solid pharmaceutical preparations. Thus, it is highly required to develop techniques of dispersing a trace unstable component in solid pharmaceutical preparations and stabilize the unstable component in the preparations in order to prevent deterioration of the preparations.

Accordingly, it is highly desirable to provide solid pharmaceutical preparations in which a vitamin $D_3$ derivative is stabilized and the content of a vitamin $D_3$ derivative is rendered uniform.

SUMMARY OF THE INVENTION

The present invention has been made in view of the foregoing disadvantage of the prior art.

The inventors have made a careful study, for the purpose of providing a composition for solid pharmaceutical preparations which is capable of permitting a vitamin $D_3$ derivative to be stabilized during the manufacture and storage and the particle size distribution and content of the vitamin $D_3$ derivative to be rendered uniform and constant, on stability of the vitamin $D_3$ derivative when it is mixed with additives (excipient, degradative agent, binder and lubricant) applicable to the preparation of solid pharmaceutical preparations. As a result, it has been found that the use of lactose, corn starch or crystalline cellulose as an excipient for the composition causes a vitamin $D_3$ to be highly decomposed, whereas the use of D-mannitol or white sugar as the excipient exhibits an effect of stabilizing the derivative.

Also, it has been found that the use of carboxymethyl cellulose as the degradative agent results in the vitamin $D_3$ derivative to be highly decomposed, whereas hydroxypropyl cellulose contributes to stabilizing of the derivative.

Thus, the present invention has been made while taking notice of the fact that solid pharmaceutical preparations obtained using mannitol and/or white sugar as a base prevents decomposition of the vitamin $D_3$ derivative.

Accordingly, it is an object of the present invention to provide a composition for solid pharmaceutical preparations containing a vitamin $D_3$ derivative which is capable of permitting the vitamin $D_3$ derivative to be significantly stabilized and the content of the derivative in the preparations to be rendered uniform.

It is another object of the present invention to provide a method of granulating a composition for solid pharmaceutical preparations containing a vitamin $D_3$ derivative which is capable of permitting the vitamin $D_3$ derivative to be significantly stabilized and the content of the derivative in the preparations to be rendered uniform.

In accordance with one aspect of the present invention, a composition for solid pharmaceutical preparations containing a vitamin $D_3$ derivative is provided. The composition comprises an excipient comprising mannitol and/or sugar; a degradative agent comprising hydroxypropyl cellulose; and/or a binder comprising polyvinyl pyrrolidone and/or hydroxypropylmethyl cellulose.

In accordance with another aspect of the present invention, a method of granulating the above-described composition. The method uses a solvent for dissolving mannitol or sugar, hydroxypropylmethyl cellulose or polyvinyl pyrrolidone, and a vitamin $D_3$ derivative.

DETAILED DESCRIPTION OF THE INVENTION

The vitamin $D_3$ derivative of the present invention includes 26, 26, 26, 27, 27, 27-hexafluoro-1α, 25-dihydroxycholecalciferol (hereinafter referred to as 'ST-630); 1α, 25-dihydroxycholecalciferol; 24, 25-dihydroxycholecalciferol; 1α-hydroxycholecalciferol; 1α, 25-dihydroxy-26, 27-hexafluorocholecalciferol; 25-hydroxycholecalciferol; 1α, 25-dihydroxy-26, 27-dimethylcholecalciferol; 1α-hydroxy-26, 27-dimethylcholecalciferol; 25-hydroxy-26, 27-dimethylcholecalciferol; 1α, 25-dihydroxy-24, 24-difluoro-26, 27-dimethylcholecalciferol; 25-hydroxy-24, 24-difluoro-26, 27-dimethylcholecalciferol; 1α, 25-dihydroxy-26, 27-diethylcholecalciferol; 25-hydroxy-26, 27-dimethylcholecalciferol; 25-hydroxy-26, 27-hexafluorocalciferol; 25-hydroxy-28-trifluorocalciferol; 25-hydroxy-26, 27-hexafluoroepicalciferol; 1α, 25-dihydroxy-24-difluorohomocholecalciferol; 1α, 25-dihydroxycholecalciferol -26, 23-lactone; 1α, 25-dihydroxy-22-oxacholecalciferol; 1α-hydroxy-22-oxacholecalciferol; and ergocalciferols corresponding to the above.

Mannitol and/or sugar used as the excipient in the composition of the present invention are loaded in an amount of from 0.1% to 99.9% by weight and preferably from 65% to 95% by weight in the composition.

Hydroxypropyl cellulose of a low degree of substitution used as the degradative agent is loaded in an amount of from 0.1% to 99.9% by weight and preferably from 5% to 30% by weight.

Polyvinyl pyrrolidone and/or hydroxypropylmethyl cellulose used as the binder is loaded in an amount of from 0.1% to 99.9% by weight and preferably from 1% to 30% by weight.

The composition for solid pharmaceutical preparations of the present invention is obtained in the form of granules. It may be prepared into pharmaceutical preparations in the form of powders, granules, pellets, capsules or tablets as it is or, if necessary, while being mixed with at least one of any suitable additives known in the art. The additives include an excipient, a degradative agent, a binder, a lubricant, an anti-oxidant, a coating agent, a coloring agent, a corrigent, a surface active agent and the like.

The excipient includes, for example, lactose, crystalline cellulose, calcium hydrogenphosphate, starch, light silica, titanium oxide, magnesium metasilicate aluminate, polyethylene glycol and the like.

The degradative agent includes, for example, carboxymethyl cellulose, calcium carboxymethylcellulose, sodium carboxymethylcellulose, croscarmellose sodium, Type A (Ac-Di-Sol ®), starch, crystalline cellulose, hydroxypropyl starch, starch partially modified into α-starch and the like.

The binder includes, for example, hydroxypropyl cellulose, gelatin, gum arabic, ethyl cellulose, polyvinyl alcohol, pullulan and the like.

The lubricant includes, for example, stearic acid, magnesium stearate, calcium stearate, talc, hardened oil, fatty saccharide and the like.

The anti-oxidant includes, for example, dibutyl hydroxytoluene (BHT), gallic propyl, butylhydroxy anisole (BHA) α-tocopherol, citric acid and the like.

The coating agent includes, for example, hydroxypropylmethyl cellulose, hydroxypropyl cellulose, methyl cellulose, ethyl cellulose, hydroxypropylmethyl cellulose phthalate, polyvinylacetal diethylaminoacetate, aminoalkyl methacrylate copolymer, hydroxypropylmethylcellulose acetate succinate, methacrylic acid coplymer, cellulose acetate trimellitate (CAT), polyvinyl acetate phthalate, and the like.

The coloring agent includes, for example, a tar pigment, titanium oxide and the like.

The corrigent includes, for example, citric acid, adipic acid, ascorbic acid, menthol and the like.

The surface active agent includes, for example, glycerin monostearate, polysorbates, sodium lauryl sulfate, lauromacrogol, fatty saccharide, and the like.

The composition for solid pharmaceutical preparations according to the present invention may be generally prepared according to a conventional wet granulation process.

A solvent used is preferably lower alcohol such as ethanol, isopropanol or the like from a viewpoint of safety in operation. Also, the granulation is preferably carried out using a solvent which is capable of dissolving all the components of the composition such as mannitol, sugar, hydroxypropyl cellulose, polyvinyl pyrrolidone and hydroxypropylmethyl cellulose, as well as a vitamin $D_3$ derivative, to thereby the composition with uniformity. In particular, it is essential to use a solvent which is capable of dissolving mannitol or sugar and a vitamin $D_3$ derivative, because a relatively large amount of excipient such as mannitol, sugar or the like is contained in the composition.

In view of the fact that mannitol and sugar are readily soluble in water but is slightly soluble in lower alcohol, the inventors have made a study on a wet granulation process using a mixed solvent of water and lower alcohol. As a result, it has been found that wet granulation of the composition using lower alcohol containing 20% or more water and preferably from 20% to 50% water permits the vitamin $D_3$ derivative to be uniformly distributed in the composition.

More particularly, the wet granulation is carried out in such a manner that mannitol and hydroxypropyl cellulose having a low degree of substitution are fully mixed together and a solution prepared by dissolving cellulose in lower alcohol containing from 20% to 50% purified water is used as a binder, to thereby provide a composition of the present invention and then the composition is dried.

As can be seen from the foregoing, the composition for solid pharmaceutical preparations of the present invention permits the vitamin $D_3$ derivative to be significantly stabilized. Also, the method of the present invention provides a composition for solid pharmaceutical preparations in which a vitamin $D_3$ derivative is uniformly contained, to thereby ensure the quality of the composition.

The present invention will be further described hereinafter with reference to the following examples and test examples.

EXAMPLE 1

11.888 kg of mannitol and 2.25 kg of hydroxypropyl cellulose of a low degree of substitution were fully mixed and pulverized to prepare a mixture, which was dried while spraying, by means of a vacuum granulation apparatus, a solution obtained by dissolving 375 g of hydroxypropylnethyl cellulose and 16.75 g of BHT in 7.125 kg of 80% ethanol onto the mixture under reduced pressure. Subsequently, the mixture was dried while spraying a solution prepared by dissolving 15 mg of ST-630 in 3.375 kg of ethanol onto the mixture under reduced pressure. Then, the mixture was dried while spraying a solution prepared by dissolving 375 g of polyvinyl pyrrolidone (hereinafter referred to as "PVP") K30 and 18.75 g of BHT in 3.375 kg of ethanol onto the mixture under reduced pressure, resulting in a composition for solid pharmaceutical preparations being obtained.

Thereafter, 0.5 part of calcium stearate was added to 99.5 parts of the composition thus obtained and then tablet preparation was carried out to obtain tablets having a diameter of 6 mm, a thickness of 3 mm and a weight of 100 mg and containing about 0.1 $\mu$g of ST-630.

EXAMPLE 2

11.888 kg of mannitol and 2.25 kg of hydroxypropyl cellulose of a low degree of substitution were fully mixed together and pulverized to prepare a mixture, which was dried while spraying, by means of a vacuum granulation apparatus, a solution obtained by dissolving 375 g of hydroxypropylmethyl cellulose and 18.75 g of BHT in 3.375 kg of 80% ethanol onto the mixture under reduced pressure. Subsequently, the mixture was dried while spraying a solution prepared by dissolving 15 mg of ST-630 in 3.375 kg of ethanol onto the mixture under reduced pressure. Then, the mixture was further dried while spraying a solution prepared by dissolving 375 g of hydroxypropylmethyl cellulose and 18.75 g of BHT in 7.125 kg of 80% ethanol onto the mixture under reduced pressure, resulting in a composition for solid pharmaceutical preparations being obtained.

Thereafter, 0.5 part of calcium stearate was added to 99.5 parts of the composition thus obtained and then tablet preparation was carried out to obtain tablets having a diameter of 6 mm, a thickness of 3 mm and a weight of 100 mg and containing about 0.1 μg of ST-630.

EXAMPLE 3

11.888 kg of mannitol and 2.25 kg of hydroxypropyl cellulose of a low degree of substitution were fully mixed together and pulverized to prepare a mixture, which was dried while spraying, by means of a vacuum granulation apparatus, a solution obtained by dissolving 0.375 kg of PVP-K30 and 18.75 g of BHT in 3.375 kg of ethanol onto the mixture under reduced pressure. Subsequently, the mixture was dried while spraying a solution prepared by dissolving 15 mg of ST-630 in 3.375 kg of ethanol onto the mixture under reduced pressure. Then, the mixture was further dried while spraying a solution prepared by dissolving 375g of PVPP-K30 and 18.75 g of BHT in 3.375 kg of ethanol onto the mixture under reduced pressure, resulting in a composition for solid pharmaceutical preparations being obtained.

Thereafter, 0.5 part of calcium stearate was added to 99.5 parts of the composition thus obtained and then tablet preparation was carried out to obtain tablets having a diameter of 6 mm, a thickness of 3 mm and a weight of 100 mg and containing about 0.1 μg of ST-630.

EXAMPLE 4

79.3 g of mannitol and 15 g of hydroxypropyl cellulose of a low degree of substitution were fully mixed together and pulverized to prepare a mixture, to which a solution obtained by dissolving 2.5 g of PVP-K30 and 0.125 g of BHT in 10 g of ethanol was added, followed by kneading and drying. Then, an ethanol solution containing 0.001 g of ST-630 was added to the mixture, which was then kneaded and dried. Subsequently, a solution obtained by dissolving 2.5 g PVP-K30 and 0.125 g of BHT in 10 g of ethanol to the mixture, which was then kneaded and dried, resulting in a composition for solid pharmaceutical preparations containing about 10 μg of ST-630 per 0.95 g of the composition.

EXAMPLE 5

793 g of mannitol and 150 g of hydroxypropyl cellulose of a low degree of substitution were fully mixed and pulverized to prepare a mixture, to which a solution obtained by dissolving 0.01 g of ST-630, 50 g of PVP-K30 and 2.5 g of BHT in 450 g of 80% ethanol was added, followed by granulation by means of a stirring granulation apparatus, resulting in a composition for solid pharmaceutical preparations. Then, the composition was dried on a fluidized bed and then pulverized. Thereafter, 5.0 g of calcium stearate was added to the composition, which was then subject to tablet preparation, to thereby prepare tablets having a diameter of 6 mm, a thickness of 3 mm and a weight of 100 mg and containing about 0.1 μg of ST-630.

EXAMPLE 6

793 g of mannitol and 150 g of hydroxypropyl cellulose of a low degree of substitution were fully mixed together and pulverized to prepare a mixture, to which a solution obtained by dissolving 0.001 g of ST-630, 50 g of PVP-K30 and 2.5 g of BHT in 450 g of 80% ethanol was added, followed by granulation. Then, the mixture was dried on a fluidized bed and pulverized. Thereafter, 5.0 g of calcium stearate was added to the mixture, which was then subject to tablet preparation, resulting in tablets which have a diameter of 6 mm, a thickness of 3 mm and a weight of 100 mg and contains about 0.1 μg of ST-630 being obtained.

EXAMPLE 7

80 g of mannitol and 15 g of hydroxypropyl cellulose of a low degree of substitution were fully mixed together and pulverized to prepare a mixture. Then, a solution obtained by dissolving 0.001 g of ST-630 and 5 g of hydroxypropyl cellulose in 30 g of 80% ethanol was added as a binder to the mixture, which was then kneaded in a mortar and dried, so that a composition containing 1 μg of ST-630 per 100 mg was obtained.

EXAMPLE 8

80 g of mannitol and 15 g of hydroxypropyl cellulose of a low degree of substitution were fully mixed together and pulverized to prepare a mixture. Then, a solution obtained by dissolving 0.001 g of ST-630 and 5 g of PVP-K30 in 45 g of 50% ethanol was added as a binder to the mixture, which was then kneaded in a mortar and dried, resulting in a composition which contains 1 μg of ST-630 per 100 mg being obtained.

EXAMPLE 9

80 g of mannitol and 15 g of hydroxypropyl cellulose of a low degree of substitution were fully mixed together and pulverized to prepare a mixture. Then, a solution obtained by dissolving 5 g of PVP-K30 in 25 g of purified water was added as a binder to the mixture, which was then kneaded and dried. Thereafter, 10 ml ethanol solution containing 1 mg of ST-630 was added to the mixture, which was fully mixed and dried, resulting in a composition which contains 1 μg of ST-630 per 100 mg being obtained.

EXAMPLE 10

80 g of mannitol and 15 g of hydroxypropyl cellulose of a low degree of substitution were fully mixed together and pulverized to prepare a mixture. Then, a solution obtained by dissolving 5 g of hydroxypropylmethyl cellulose in 45 g of purified water was added as a binder to the mixture, which was then kneaded and dried. Thereafter, 10 ml ethanol solution containing 1 mg of ST-630 was added to the mixture, which was fully mixed and dried, resulting in a composition which contains 1 μg of ST-630 per 100 mg being obtained.

EXAMPLE 11

80 g of mannitol and 15 g of hydroxypropyl cellulose of a low degree of substitution were fully mixed together and pulverized to prepare a mixture. Then, a solution obtained by dissolving 1 mg of ST-630, 5 g of PVP-K30 and 0.25 g of BHT in 45 g of 80% ethanol was added to the mixture, which was then kneaded in a mortar and dried, resulting in a composition which contains 1 μg of ST-630 per 100 mg being obtained.

EXAMPLE 12

76.25 g of mannitol and 14 g of hydroxypropyl cellulose of a low degree of substitution were fully mixed together and pulverized to prepare a mixture. Then, a solution obtained by dissolving 5 g of PVP-K30 and 0.25 g of BHT in 30 g of ethanol was added to the mixture, which was then kneaded and dried. Thereafter, 10 ml ethanol solution containing 1 mg of ST-630 was added to the mixture, which was fully mixed and dried, resulting in a composition which contains about 10 μg of ST-630 per 0.955 g being obtained.

Test Example 1 (Test on uniformity of content)
(Specimen)
Specimen No. 1: 1 μg tablet prepared in Example 5
Specimen No. 2: 0.1 μg tablet prepared in Example 6
(Test Procedure)
Specimen No. 1:

To one tablet of specimen No. 1 was accurately added an internal standard solution (1) in a volume of 1 ml, which was then subject to an ultrasonic treatment for 30 minutes, followed by a centrifugal treatment (3000 rpm) for 10 minutes to obtain a supernatant. Then, the supernatant was passed through a membrane filter to obtain a sample solution (n=10). 50 ml sample solution was subject to determination described hereinafter, so that a peak area of ST-630 relative to a peak area of the internal standard substance was obtained to calculate an average deviation in n=10.

Specimen No. 2:

To one tablet of specimen No. 2 was accurately added 0.5 ml water, which was then subject to an ultrasonic treatment for 10 minutes. Then, an internal standard solution (2) was added in a volume of 0.5 ml thereto, which was then subject to an ultrasonic treatment for 20 minutes and a centrifugal treatment (3000 rpm) for 10 minutes to obtain a supernatant. Then, the supernatant was passed through a membrane filter to obtain a sample solution (n=10). 50 ml sample solution was subject to liquid chromatography as described hereinafter, so that a peak area of ST-630 relative to a peak area of the internal standard substance was obtained to calculate an average deviation in n=10.

Internal standard solution (1): Estradiol benzoate 4 μg/ml
Internal standard solution (2): Estradiol benzoate 0.5 g/ml Operating Conditions Detector: Ultraviolet absorptiometer (wavelength for measurement: 265 nm)
Column: Stainless tube of 4 mm in inner diameter and 15 mm in length (SK-GEL, ODS-80TM)
Temperature: 50° C.
Mobile phase: methanol:water (77:23)
(Result)
Results were as indicated in Table 1.

TABLE 1

| (Test on uniformity of content) | | |
|---|---|---|
| | Deviation (%) | |
| No. | Specimen No. 1 | Specimen No. 2 |
| 1 | 0.5 | 6.4 |
| 2 | 1.9 | 1.3 |
| 3 | 1.1 | 2 6 |
| 4 | 1.9 | 2.3 |
| 5 | 2.2 | 1.5 |
| 6 | 0.8 | 2.2 |
| 7 | 1.3 | 0.1 |

TABLE 1-continued

| (Test on uniformity of content) | | |
|---|---|---|
| | Deviation (%) | |
| No. | Specimen No. 1 | Specimen No. 2 |
| 8 | 0.4 | 4.2 |
| 9 | 1.9 | 2.8 |
| 10 | 0.5 | 3.7 |
| Maximum Deviation | 2.2 | 6.4 |

Test Example 2 (Test on change with time)
(Specimen)
Specimen No. 1: Lactose (Japanese Pharmacopoeia)
Specimen No. 2: Corn starch (Japanese Pharmacopoeia)
Specimen No. 3: Crystalline cellulose (Japanese Pharmacopoeia)
No. 4: D-mannitol (Japanese Pharmacopoeia)
Specimen No. 5: White sugar (Japanese Pharmacopoeia)
Specimen No. 6: Anhydrous lactose (Japanese Pharmacopoeia)
Specimen No. 7: Calcium carboxymethylcellulose (Japanese Pharmacopoeia)
Specimen No. 8: Hydroxypropylmethyl cellulose of low degree of substitution (Japanese Pharmacopoeia)
(Preparation of sample)

5 ml ethanol solution containing ST-63 in a concentration of 100 μg/ml was added to 50 g of each of the specimens and mixed therewith in a mortar to prepare a mixture. Then, the mixture was dried at 70° C. and passed through a 50-mesh screen, resulting in obtaining a sample.

(Test procedure)

5 g of each of the samples obtained as described above was sealedly placed in a 4K glass bottle and stored at a temperature of 40° C.

(Determination procedure)

Each of the samples was precisely weighed in an amount of 1 g and 4 ml internal standard solution (1) was accurately added to the weighed sample, which was then subject to an ultrasonic treatment for 30 minutes, vibration for 10 minutes and a centrifugal treatment (3000 rpm) for 10 minutes in order, to thereby obtain a supernatant. Then, the supernatant was passed through a membrane filter, resulting in a sample solution.

About 20 mg of ST-630 was precisely weighed and methanol was added to the weighed ST-630, resulting in a solution of 20 ml in total volume. The solution was accurately sampled in a volume of 5 ml and the internal standard solution (2) was accurately added in a volume cf 2 ml to the sampled solution. Then, the mobile phase was accurately added thereto until the total volume accurately reaches 20 ml, resulting in a standard solution (1) for Specimen No. 1.

50 μl of each of the sample solutions and standard solutions was subject to liquid chromatography to obtain peak areas $Q_t$ and $Q_s$ of ST-630 relative to a peak area of the internal standard substance.

Internal standard solution (1): Estradiol benzoate 10 μg/ml
Internal standard solution (2): Estradiol benzoate 100 μg/ml Then, the content of T-630 in 1 g of the sample was calculated according to the following expression:

Amount of ST-630 (μg) contained in 1 g of sample
= 10(μg) × amount of standard ST-630 (mg)
× $Q_t/Q_s$ × 50/the amount of sample (mg)

(Result)
The results were as indicated in Table 2.

TABLE 2

| Specimen | After 1 month | After 2 months | After 3 months | After 6 months |
|---|---|---|---|---|
| 1 | 64.2 | 46.2 | 38.2 | 18.6 |
| 2 | 73.5 | 59.8 | 36.9 | 14.7 |
| 3 | 86.4 | 67.5 | 49.3 | 32.1 |
| 4 | 93.0 | 90.4 | 88.4 | 81.3 |
| 5 | 91.7 | 97.2 | 94.3 | 92.2 |
| 6 | 70.9 | — | — | 26.2 |
| 7 | 77.9 | 58.9 | 43.7 | 26.8 |
| 8 | 99.2 | — | 100.0 | 91.2 |

Test Example 3 (Test on change with time) (Specimen)

Specimen No. 1: 0.1 μg tablet prepared in Example 1
Specimen No. 2: 0.1 μg tablet prepared in Example 2
Specimen No. 3: 0.1 μg tablet prepared in Example 3
Specimen No. 4: Composition prepared in Example 4
Specimen No. 5: 1 μg tablet prepared in Example 5
Specimen No. 6: 0.1 μg tablet prepared in Example 6
Specimen No. 7: Composition prepared in Example 11
Specimen No. 8: Composition prepared in Example 12
Reference specimen: Composition obtained by adding an ethanol solution containing ST-630 in concentration of 100 μg/ml to 50 g of lactose, followed by drying in a mortar.

(Test procedure) 50 pieces of each of the specimens in the form of a tablet and 5 g of each of the specimens in the form of a composition each were sealedly placed in a 4K glass bottle and stored at a temperature of 40° C.

(Determination procedure)
Liquid specimen No. 1: 10 tablets of Specimen No. 1 were sampled and an internal standard solution (1) was accurately added thereto.
Liquid specimen No. 2: 10 tablets of Specimen No. 2 were sampled and the internal standard solution (1) was accurately added in a volume of 2 ml thereto.
Liquid specimen No. 3: 10 tablets of Specimen No. 3 were sampled and the internal standard solution (1) was accurately added in a volume of 2 ml thereto.
Liquid specimen No. 4: 1 g of Specimen No. 4 was sampled and an internal standard solution (2) was accurately added in a volume of 4 ml thereto.
Liquid specimen No. 5: 10 tablets of Specimen No. 5 were sampled and the internal standard solution (2) was accurately added in a volume of 4 ml thereto.
Liquid specimen No. 6: 10 tablets of Specimen No. 6 were sampled and the internal standard solution (1) was accurately added in a volume of 2 ml thereto.
Liquid specimen No. 7: 1 g of Specimen No. 7 was sampled and the internal standard solution (2) was accurately added in a volume of 4 ml thereto.
Liquid specimen No. 8: 1 g of Specimen No. 8 was sampled and the internal standard solution (2) was accurately added in a volume of 4 ml thereto.
Reference liquid specimen: 1 g of the reference specimen was precisely weighed and the internal standard solution (2) was accurately added in a volume of 4 ml thereto.

Each of the liquid specimens prepared as described above was subject to an ultrasonic treatment for 30 minutes, vibration for 10 minutes and a centrifugal treatment for 10 minutes in order, to thereby obtain a supernatant. Then, the supernatant was passed through a membrane filter, resulting in a sample solution being obtained.

Also, about 20 mg of ST-630 was precisely weighed and methanol was added thereto, resulting in the total volume being accurately 20 ml. The so-prepared solution was accurately sampled in a volume of 1 ml and a mobile phase was added thereto, resulting in a solution of accurately 100 ml in total volume. Then, the solution was accurately sampled in a volume of 5 ml and an internal standard solution (2) was accurately added in a volume of 2 ml thereto and further the mobile phase was added thereto to cause the total volume to be accurately 20 ml. This resulted in a standard solution (1) for each of Specimens No. 1, No. 2, No. 3 and No. 6.

Further, the standard solution (1) was accurately sampled in a volume of 4 ml and the mobile phase was added thereto, to thereby cause the total volume to be accurately 20 ml. This resulted in a standard solution (2) for each of Specimens No. 1, No. 2, No. 3 and No. 6.

Internal standard solution (1): Estradiol benzoate 2 μg/ml
Internal standard solution (2): Estradiol benzoate 10 μg/ml
Internal standard solution (3): Estradiol benzoate 100 μg/ml 50 μl of each of the sample solutions and standard solution was subject to liquid chromatography to obtain peak areas $Q_t$ and $Q_s$ of ST-630 relative to a peak area of the internal standard substance.

Then, the content of ST-630 in 1 g of the specimen was calculated according to each of the following expressions:

Expression

For each of Specimens No. 4, No. 5, No. 7 and No. 8 and
Reference specimen:

Amount of ST-630 (μg) contained in 1 g of specimen =
10 (μg) × amount of standanrd ST-630 (mg) ×
$Q_t/Q_s$ × 50/the amount of sample (mg)

For each of Specimens No. 1, No. 2, No. 3 and No. 6:

Amount of ST-630 (μg) contained in 1 g of specimen =
1 (μg) × amount of standanrd ST-630 (mg) ×
$Q_t/Q_s$ × 50/the amount of sample (mg)

Operating Conditions

Detector: Ultraviolet absorptiometer (wavelength for measurement: 265 nm)
Column: Stainless tube of 4 mm in inner diameter and 15 mm in length (SK-GEL, ODS-80TM)
Column temperature: 50° C.
Mobile phase: methanol : water (77:23)
(Result)
The results were as indicated in Table 3.

TABLE 3

| Specimen | After 1 month | After 2 months | After 3 months |
| --- | --- | --- | --- |
| Reference | 64.2 | 46.2 | 38.2 |
| 1 | 103.8 | 100.5 | 99.1 |
| 2 | 102.3 | 100.3 | 99.0 |
| 3 | 100.5 | 100.0 | 96.7 |
| 4 | 100.4 | 100.0 | 100.8 |
| 5 | 99.0 | 96.5 | 97.6 |
| 6 | 99.0 | 97.6 | 100.9 |
| 7 | 98.3 | 98.6 | 98.0 |
| 8 | 98.4 | 98.8 | 98.0 |

What is claimed is:

1. A granule consisting essentially of:
    (A) a main component of 26, 26, 26, 27, 27, 27-hexafluoro-1α25- dihydroxycholecalciferol;
    (B) an excipient of 65 to 95% by weight selected from the group consisting of mannitol and sugar;
    (C) a degradative agent of 5 to 30% by weight of hydroxypropyl cellulose having a low degree of substitution; and
    (D) a binder of 1 to 30% by weight selected from the group consisting of polyvinyl pyrrolidone and hydroxymethyl cellulose.

* * * * *

UNITED STATES PATENT AND TRADEMARK OFFICE
CERTIFICATE OF CORRECTION

PATENT NO. : 5,328,903
DATED : July 12, 1994
INVENTOR(S) : Ishii et al

It is certified that error appears in the above-indentified patent and that said Letters Patent is hereby corrected as shown below:

IN THE CLAIMS:

Claim 1
Col. 12, line 4          Delete "1α25" and substitute therefor ---1α,25---

Signed and Sealed this

Twenty-fifth Day of April, 1995

*Attest:*

BRUCE LEHMAN

*Attesting Officer*          *Commissioner of Patents and Trademarks*